United States Patent [19]
Jones et al.

[11] Patent Number: 5,202,094
[45] Date of Patent: Apr. 13, 1993

[54] SPECIMEN CUP HOLDER

[76] Inventors: Timothy B. Jones, 3030 SW. 89, Apt. #E, Oklahoma City, Okla. 73159; Robert D. Jones; Lori D. Jones, both of 1452 N. Washington, Ardmore, Okla. 73401

[21] Appl. No.: 776,627

[22] Filed: Oct. 15, 1991

[51] Int. Cl.$^5$ .............................................. B01L 3/00
[52] U.S. Cl. ................... 422/102; 422/103; 422/104; 215/100 A; 220/737; 220/758; 220/759; 229/1.5 H; 16/110.5; 16/114 R
[58] Field of Search ............... 422/102, 103, 104, 99; 206/217; 215/100 A; 220/96, 94 R, 703, 737, 738; 229/1.5 H; 16/114 R, 110.5, 113

[56] References Cited
U.S. PATENT DOCUMENTS

| | | | |
|---|---|---|---|
| 2,285,698 | 6/1942 | Emmer | 16/114 R |
| 3,088,767 | 5/1963 | Deal | 215/100 A |
| 4,552,276 | 11/1985 | Büch | 220/737 X |

Primary Examiner—James C. Housel
Assistant Examiner—Maureen M. Wallenhorst
Attorney, Agent, or Firm—Glen M. Burdick

[57] ABSTRACT

An specimen cup holder is provided which permits a person to position a conventional specimen gathering device, such as a specimen cup, for receipt of a specimen without contact with the specimen. The specimen cup holder is provided with a specimen cup engaging assembly having a handle member connectable thereto such that the handle member extends outwardly from the specimen cup engaging assembly. The connector assembly, which connects the handle member to the specimen cup engaging assembly, is provided with a female member and a male member. The interconnection of the handle member to the specimen cup engaging assembly via the male and female members of the connector assembly enables a person to grasp a gripping portion of the handle member and easily position the specimen cup for receipt of the specimen.

15 Claims, 4 Drawing Sheets

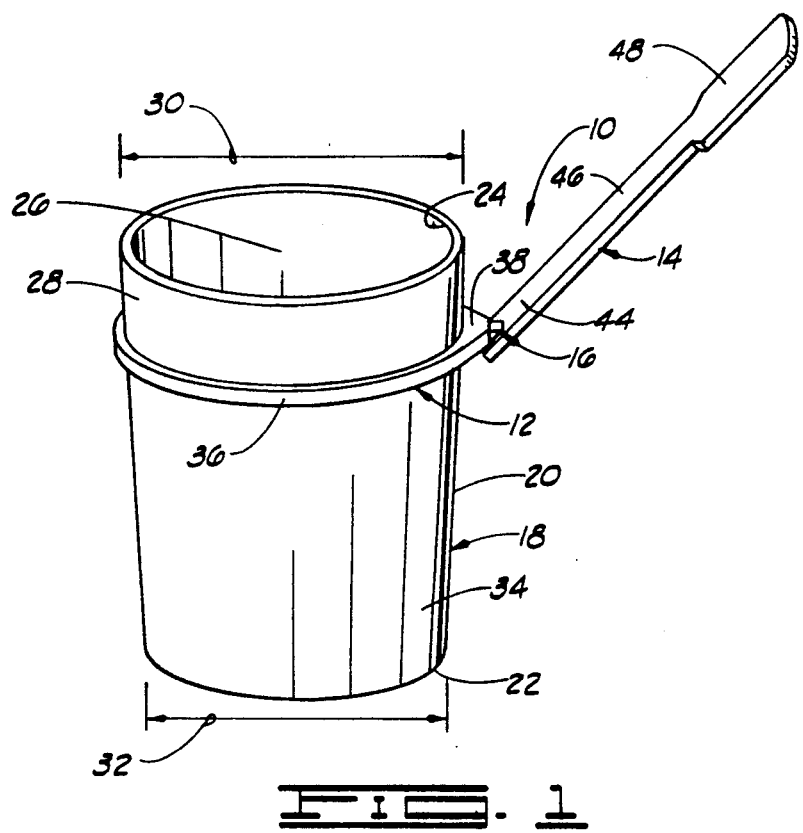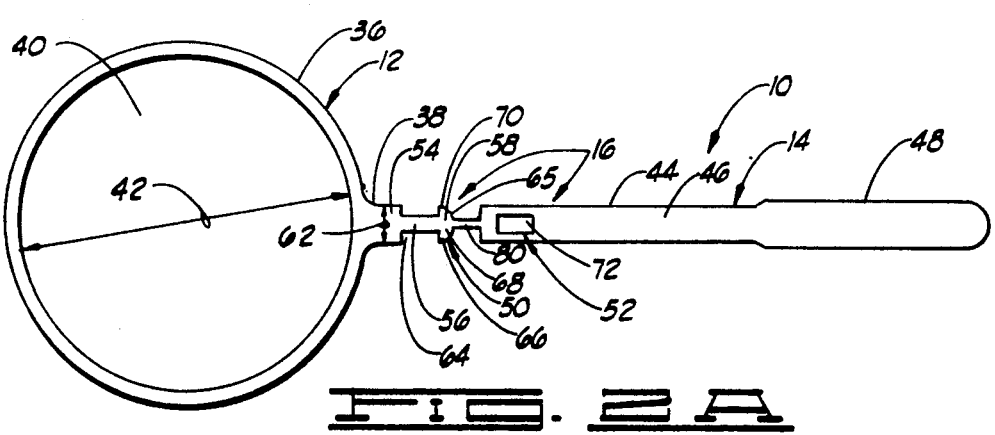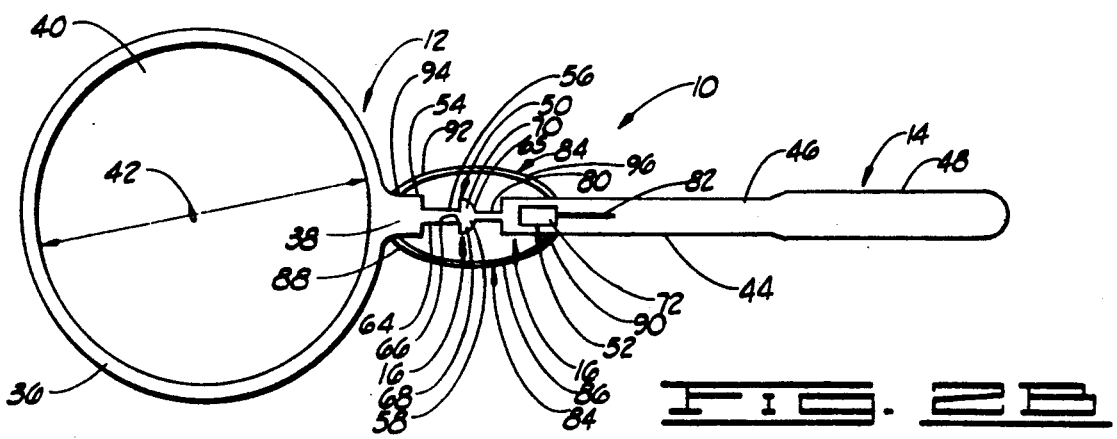

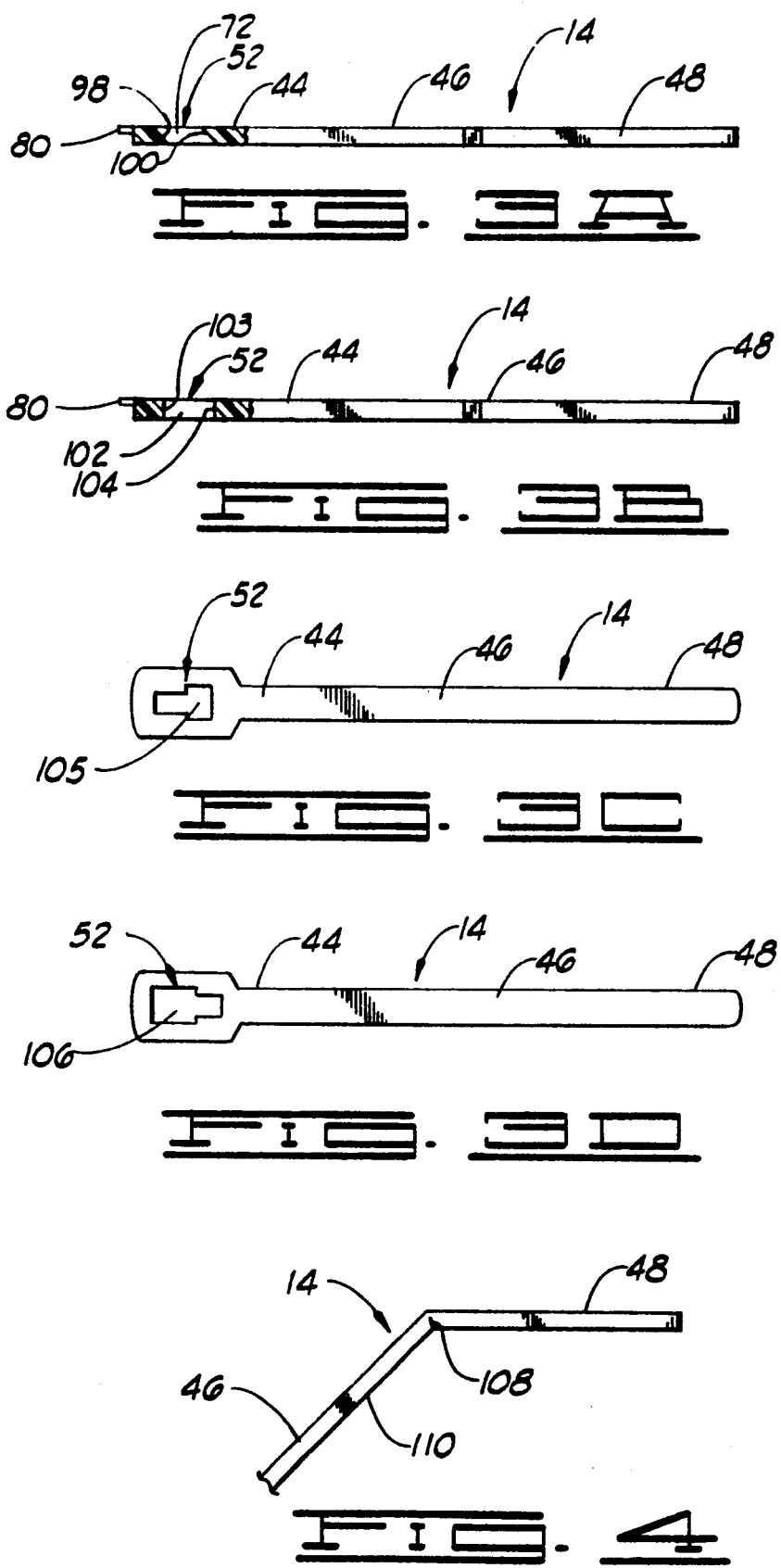

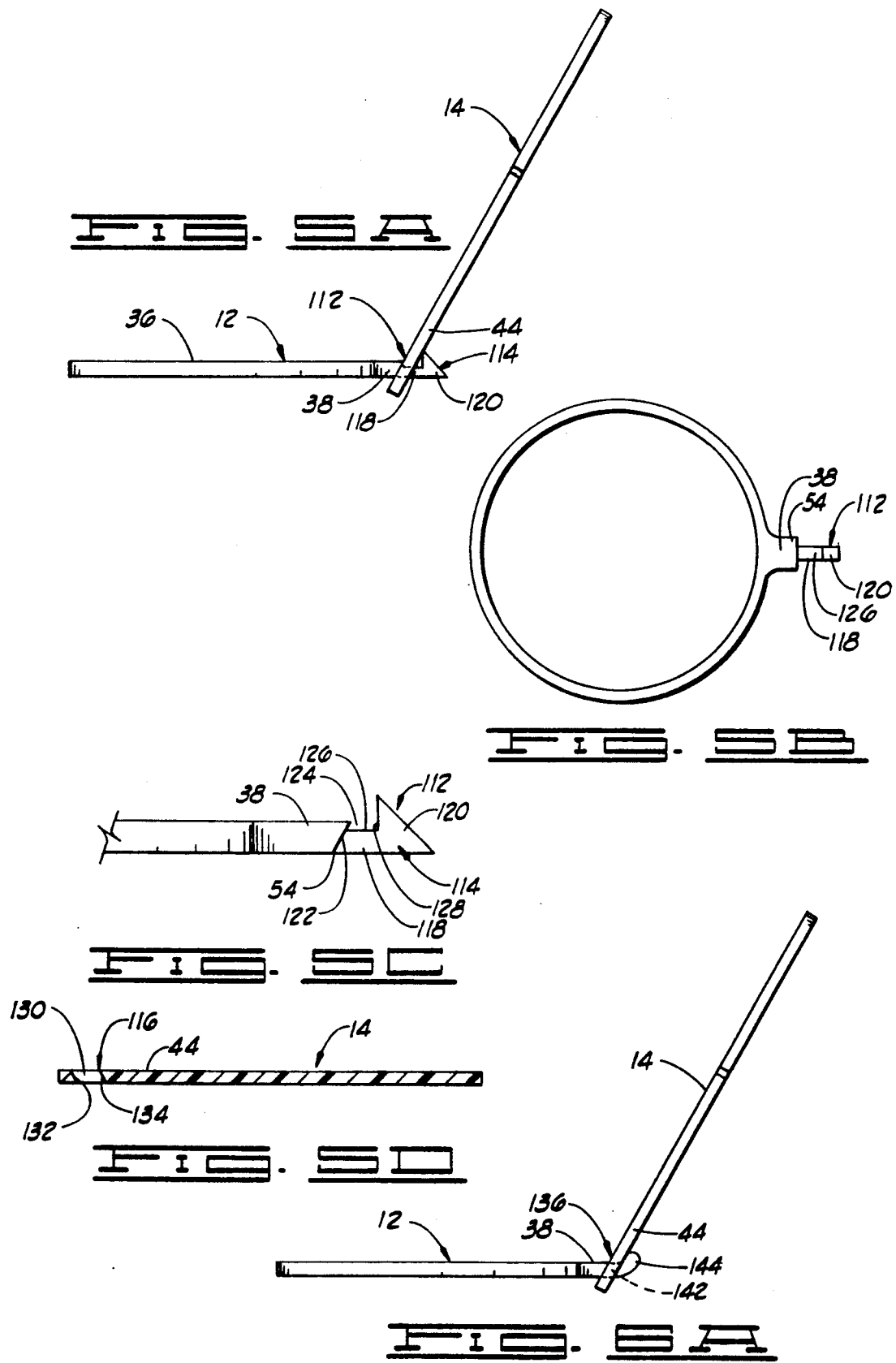

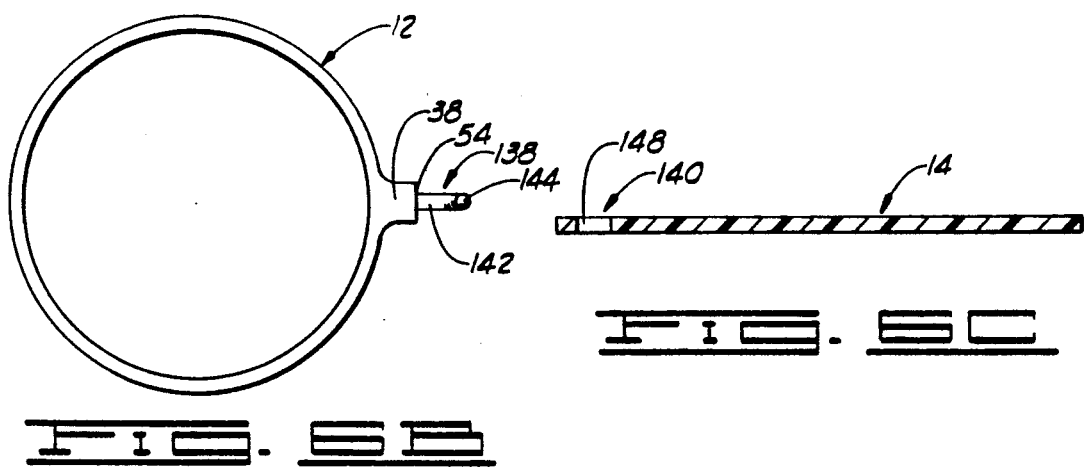
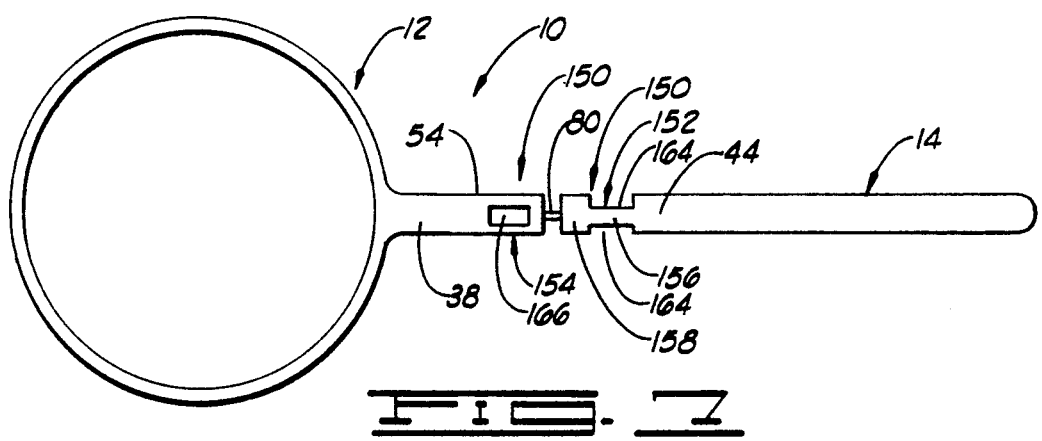
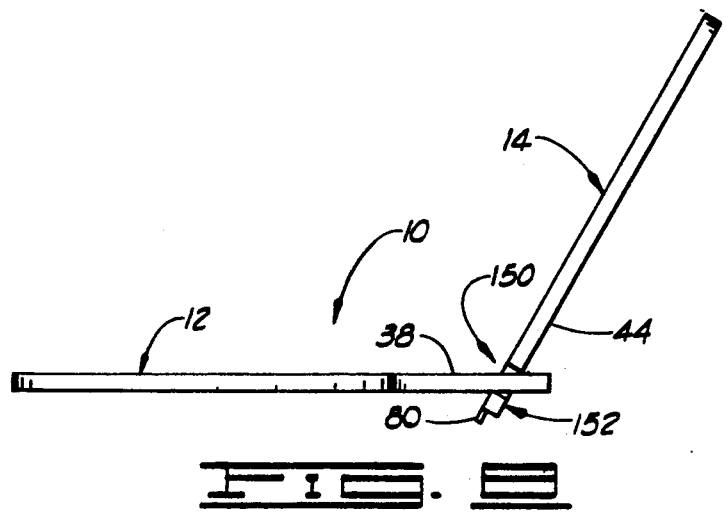

5,202,094

1

SPECIMEN CUP HOLDER

BACKGROUND OF THE INVENTION

1. Field of the Invention

The present invention relates to specimen gathering devices, and more particularly but not by way of limitation to an improved holder for a specimen cup.

2. Brief Description of the Prior Art

Specimen cups and other specimen gathering devices have heretofore found wide use in the medical profession for obtaining specimens, such as urine, which must be analyzed to diagnose illnesses prior to implementing a desired medical treatment. The procedure for obtaining a specimen is often difficult and unpleasant because the person gathering the specimen often comes into contact with the specimen.

The unpleasant and often difficult process involved in gathering a specimen has been overcome to a large extent by the improved specimen cup and holder disclosed in our copending U.S. patent application Ser. No. 07/679,267 filed Apr. 2, 1991. The holder disclosed in Ser. No. 07/679,267 also provides improved stability to the specimen cup during receipt of the specimen. However, a need remains for a specimen cup holder for a conventional specimen cup which is simple in construction and economical to manufacture, while at the same time permitting persons of all ages to assemble the specimen cup holder and to employ same to support the specimen cup. It is to such an improved specimen cup holder that the subject invention is directed.

SUMMARY OF THE INVENTION

The present invention relates to an improved specimen cup holder which permits a person to position a conventional specimen gathering device, such as a specimen cup, for receipt of a specimen without contact with the specimen. Broadly, the specimen cup holder comprises a specimen cup engaging assembly having a handle member connectable thereto such that the handle member extends outwardly from the specimen cup engaging assembly. The specimen cup engaging assembly is constructed so as to supportingly receive the specimen cup in a stable, specimen-receiving position; and because the handle member extends outwardly from the specimen cup engaging assembly, a person can more easily position the specimen cup supported by the specimen cup engaging assembly for receipt of the specimen.

The improved specimen cup holder of the present invention further comprises a connector assembly for connecting the handle member to the specimen cup engaging assembly. The connector assembly is comprised of a female member and a male member. One of the female or male members is supported by an extension member of the specimen cup engaging assembly and the other of the female and male members is supported by one end portion of the handle member. Thus, in a connected position, a distal end portion of the handle defines a gripping portion which is disposed outwardly from the specimen cup engaging assembly and thus the specimen cup supported therein. That is, the interconnection of the handle member to the specimen cup engaging assembly enables a person to grasp the gripping portion of the handle member and easily position the specimen cup for receipt of the specimen without fear of contacting the specimen.

2

An object of the present invention is to provide an improved specimen cup holder adapted to supportingly receive a specimen cup which will permit a person to quickly and easily position the specimen cup for receipt of a specimen.

Another object of the present invention, while achieving the before-stated object, is to provide a specimen cup holder adapted to support a specimen cup which substantially eliminates contact with the specimen during gathering of the specimen in the specimen cup.

Yet another object of the present invention, while achieving the before stated objects, is to provide an improved specimen cup holder which is economical to manufacture, durable in construction, easy to use and which overcomes many of the problems heretofore present in the use of the prior art specimen gathering devices.

Other objects, features and advantages of the present invention will become clear upon reading the following detailed description in conjunction with the drawings and the appended claims.

BRIEF DESCRIPTION OF THE DRAWINGS

FIG. 1 is a perspective view of a specimen cup holder constructed in accordance with the present invention, the specimen cup holder being in an assembled position and supportingly engaging a specimen cup.

FIG. 2A is a top plan view of the specimen cup holder of FIG. 1 in a non-assembled position.

FIG. 2B is a top plan view of a second embodiment of a specimen cup holder constructed in accordance with the present invention in a non-assembled position.

FIG. 3A is a side elevational view, partially in cross section, illustrating one embodiment of a female member of a connector assembly of a specimen cup holder constructed in accordance with the present invention, the female member supported by one end portion of a handle member of the specimen cup holder.

FIG. 3B is a side elevational view, partially in cross section, illustrating a second embodiment of a female member of a connector assembly of a specimen cup holder of the present invention, the female member supported by one end portion of a handle member of the specimen cup holder.

FIG. 3C is a top plan view of a handle of the specimen cup holder of the present invention having a substantially T-shaped opening in one end thereof which forms the female connector of the connector assembly for connecting the handle member to a specimen cup receiving assembly.

FIG. 3D is another embodiment of the opening in one end of the handle member which functions as the female member of the connector assembly for connecting the handle member to the specimen cup engaging assembly.

FIG. 4 is an enlarged, side elevational view of a handle member of the specimen cup holder of the present invention, the handle member having a hinge formed via a lower surface thereof such that a distal end portion of the handle member can be angularly disposed relative to an elongated axis of the handle member to assist in positioning a specimen cup for receipt of a specimen.

FIG. 5A is a second embodiment of a specimen cup holder constructed in accordance with the present invention.

FIG. 5B is a top plan view of a specimen cup engaging assembly of the specimen cup holder of FIG. 5A wherein a handle member has been removed.

FIG. 5C is an enlarged, fragmental side elevational view of a portion of the specimen cup engaging assembly of the specimen cup holder of FIG. 5A illustrating a male member of a connector assembly for detachably connecting the handle member to the specimen cup engaging assembly.

FIG. 5D is a side elevational view, partially in cross section, of a handle member of the specimen cup holder of FIG. 5A.

FIG. 6A is a side elevational view of another embodiment of a specimen cup holder constructed in accordance with the present invention.

FIG. 6B is a top plan view of a specimen cup engaging assembly of the specimen cup holder of FIG. 6A wherein a handle member has been removed.

FIG. 6C is a side elevational view, partially in cross section, of a handle member of the specimen cup holder of FIG. 6A.

FIG. 7 is a top plan view of a specimen cup holder constructed in accordance with the present invention wherein the specimen cup holder is in its non-assembled position.

FIG. 8 is a side elevational view of the specimen cup holder of FIG. 7 in its assembled position.

DESCRIPTION

In the drawings, like elements will be designated by the same numerals throughout.

Referring now to the drawings and more particularly to FIGS. 1, 2A and 2B, shown therein is an improved specimen cup holder 10 constructed in accordance with the present invention. The specimen cup holder 10 comprises a specimen cup engaging assembly 12 and a handle member 14. The handle member 14 is connected to the specimen cup engaging assembly 12 by a connector assembly 16 such that the handle member 14 is angularly disposed relative to the specimen cup engaging assembly 12. That is, the handle member extends outwardly and upwardly from the specimen cup engaging assembly 12 substantially as shown in FIG. 1.

The specimen cup holder 10 of the present invention affords numerous advantages. For example, the specimen cup engaging assembly 12 of the specimen cup holder 10 is adapted to supportingly receive a specimen gathering device, such as a specimen cup 18, so that a person can collect a specimen in the specimen cup 18 without contact with the specimen. In addition, the unique design and construction of the specimen cup holder 10 enhances the production and packaging of the specimen cup holder 10.

The specimen cup 18 is of conventional construction and comprises a continuous tapered side wall 20 and a bottom member 22. The continuous side wall 20 is tapered from an open upper end 24 towards the bottom member 22 so as to define a specimen receiving cavity 26. Thus, an upper portion 28 of the specimen cup 18 has a diameter 30 greater than the diameter 32 of a lower portion 34 of the specimen cup 18.

While the specimen cup 18 has been illustrated as having an inverted, substantially frusto-conical configuration, it is to be understood that the specimen cup 18 can be constructed in a variety of shapes and configurations. Further, the specimen cup 18 can be fabricated of any suitable substantially fluid-impervious material, such as plastic, glass and the like.

As is more clearly shown in FIGS. 2A and 2B, the specimen cup engaging assembly 12 comprises a ring member 36 and an extension member 38. The ring member 36 is provided with an opening 40 therein for receiving and supportingly engaging the side wall 20 of the specimen cup 18. The internal diameter 42 of the ring member 36 is greater than the diameter 32 of the lower portion 34 of the specimen cup 18, but less than the diameter 30 of the upper portion 28 of the specimen cup 18. Thus, when the specimen cup 18 is positioned within the opening 40 of the ring member 36, the ring member 36 frictionally engages a portion of the tapered side wall 20 of the specimen cup 18 and secures the specimen cup 18 in a stable, specimen-receiving position.

The configuration of the opening 40 of the ring member 36 can be provided with a variety of configurations, and the configuration of the opening 40 will depend upon the configuration of the specimen cup 18. The only critical feature as to the configuration of the opening 40 of the ring member 36 is that it have a shape and diameter to receive a portion of the specimen cup 18 therein, while at the same time frictionally engaging the side wall 20 of the specimen cup 18 so that the specimen cup 18 can be secured in a stable, specimen-receiving position when disposed within the opening 40 of the ring member 36.

The handle member 14, which is detachably connectable to the extension member 38 of the specimen cup engaging assembly 12, is characterized as have a first end portion 44, a medial or body portion 46, and an opposed second end portion 48. The first end portion 44 of the handle member 14 is connected to the extension member 38 of the specimen cup engaging assembly 12 via the connector assembly 16 such that the medial portion 46, and thus the opposed second end portion 48 of the handle member 14, are angularly disposed relative to the plane of the ring member 36. That is, the handle member 14 extends upwardly and outwardly from the ring member 36 of the specimen cup engaging assembly 12 substantially as shown. Thus, when the handle member 14 is connected to the extension member 38, and the specimen cup 18 is supported by the ring member 36, the opposed second end portion 48 of the handle member 14 defines a gripping portion so that a person can readily position the specimen cup 18 for receipt of a specimen without contact with the specimen.

The connector assembly 16 for connecting the first end portion 44 of the handle member 14 to the extension member 38 of the specimen cup engaging assembly 12 comprises a male member 50 and a female member 52. The male member 50 can be supported by a distal end 54 of the extension member 38 of the specimen cup engaging assembly 12 and the female member 52 can be supported by the first end portion 44 of the handle member 14 (substantially as shown in FIGS. 1-3D and 5A-6C); or, the male member 50 can be supported by the first end portion 44 of the handle member 14 and the female member 52 can be supported by the distal end 54 of the extension member 38 of the specimen cup engaging assembly 12 (substantially as shown in FIGS. 7 and 8). Further, the male and female members, 50 and 52, respectively, can be of any suitable configuration provided that the female member 52 is adapted to matingly receive and retain the male member 50 so that the first end portion 44 of the handle member 14 can be connected in a stable position to the extension member 38 of the specimen cup engaging assembly 12.

The male member 50 of the connector assembly 16 (FIGS. 2A-2B) extends from the distal end 54 of the extension member 38. The male member 50 is provided with a body portion 56 and an enlarged head portion 58. The body portion 56 has a width which is less than the width of the extension member 38. Thus, a recess 64 is formed between the distal end 54 of the extension member 38 and the enlarged head portion 58 of the male member 50.

A forward extending portion 65 of the enlarged head portion 58 is provided with an arcuate configuration; and a rearwardly extending portion 66 of the enlarged head portion 58 defines outwardly extending retaining members 68, 70. The arcuate configuration of the forward extending end portion 65 enables one to more easily insert the male member 50 into the female member 52 of the connector assembly 16, and the retaining members 68, 70 secure the male member 50 to the female member 52 by abuttingly engaging the female member 52. That is, when the body portion 56 of the male member 50 is disposed in the female member 52, the enlarged head portion 58 of the male member 50 is secured to the female member 52 because the retaining members 68, 70 of the enlarged head portion 58 engage the female member 52 and prevent inadvertent and unintentional removal of the handle member 14 from the extension member 38 of the specimen cup engaging assembly 12.

The female member 52 of the connector assembly 16 (which is supported by the first end portion 44 of the handle member 14 in FIGS. 1-3D and 5A-6B) includes a slot or opening 72 having a width substantially corresponding to the width of the body portion 56 of the male member 50 and a length substantially corresponding to the width of the enlarged head portion 58 of the male member 50. Thus, in order to connect the handle member 14 to the extension member 38 of the specimen cup engaging assembly 12, one first separates the handle member 14 from the extension member 38 by breaking a linkage 80 extending between the male member 50 and the female member 52 of the connector assembly 16. Thereafter, the handle member 14 is rotated approximately 90° so that the enlarged head portion 58 of the male member 50 is aligned with the length of the slot 72.

The enlarged head portion 58 of the male member 50 is then positioned through the slot 72 and thereafter the handle member 14 is again rotated 90° so that the retaining members 68, 70 formed on the rearwardly extending portion 66 of the enlarged head portion 58 abuttingly engage the portion of the female connector member 52 adjacent the slot 72 and secures the handle member 14 to the extension member 38 of the specimen cup engaging assembly 12.

In order to assist in positioning the enlarged head portion 58 of the male member 50 through the slot 72 of the female member 52, the handle member 14 can be provided with a slit 82 (FIG. 2B) in the first end portion 44 thereof. The slit 82 openly communicates with the slot 72 of the female connector member 52. The slit 82 enables one to more easily distort the slot 72 for insertion of the enlarged head portion 58 of the male member 50 into the slot 72 when connecting or disconnecting the handle member 14 and the extension member 38 of the specimen cup engaging assembly 12.

Referring now to FIG. 2B, the specimen cup holder 10 is illustrated as further comprising a second connector assembly 84 for connecting the first end portion 44 of the handle member 14 to the extension member 38 of the specimen cup engaging assembly 12 when the handle member 14 has been separated by breakage of the linkage 80. That is, the second connector assembly 84 connects the first end portion 44 of the handle member 14 to the extension member 38 of the specimen cup engaging assembly 12 when same are in a disassembled position, while permitting the handle member 14 to be selectively rotated in order to connect the handle member 14 to the extension member 38 via the male and female members, 50 and 52, respectively, of the connector assembly 16.

The second connector assembly 84 comprises a first connector member 86 having a first end 88 and an opposed second end 90, and a second connector member 92 having a first end 94 and an opposed second end 96. The first end 88 of the first connector member 86 is connected to one side of the extension member 38 of the specimen cup engaging assembly 12 and the opposed second end 90 of the first connector member 86 is connected to the first end portion 44 of the handle member 14, substantially as shown in FIG. 2B.

Similarly, the first end 94 of the second connector member 92 is connected to a second side of the extension member 38 of the specimen cup engaging assembly 12 and the opposed second end 96 of the second connector member 92 is connected to the first end portion 44 of the handle member 14 substantially as shown in FIG. 2B.

The first and second connector members 86, 92 are provided with a length sufficient so that upon separation of the handle member 14 from the extension member 38 by breakage of the linkage 80, the first and second connector members 86, 92 maintain a connection between the handle member 14 and the extension member 38, while permitting the handle member 14 to be sufficiently rotated to permit placement of the enlarged head portion 58 of the male member 50 into the slot 72 of the female member 52 so that the handle member 14 can be connected to the extension member 38 via the male and female members 50, 52 of the connector assembly 16.

Referring now to FIG. 3A, the slot 72 of the female member 52 is illustrated as having a first end 98 and an opposed second end 100. The first and second ends 98, 100 of the slot 72 are beveled and substantially parallel so that when the male member 50 is matingly engaged with the female member 52 of the connector assembly 16, the handle member 14 is supported in a desired angular position relative to the ring member 36 of the specimen cup engaging assembly 12.

FIG. 3B illustrates another embodiment of a slot 102 of the female connector member 52. The slot 102 is provided with first and second end portions 103 and 104. The first and second end portions 103, 104 of the slot 102 are substantially parallel to each other and are disposed perpendicular to the elongated axis of the handle member 14.

Referring now to FIGS. 3C and 3D, the female member 52 of the connector assembly 16 is illustrated as having slots of varying configurations. That is, the female member 52 is illustrated, in FIG. 3C, as having a substantially T-shaped slot 105; whereas the female member 52 of the connector assembly 16 depicted in FIG. 3D is provided with a slot 106 having an inverted, substantially keyhole-shaped configuration.

To further assist in positioning the specimen cup 18 for receipt of a specimen (without contact with the specimen by a person holding the handle 14 of the specimen cup holder 10), the handle member 14 is desirably provided with a V-shaped groove 108 formed in a lower surface 110 of the handle member 14 at the junction between the medial portion 46 and the opposed second end portion 48 of the handle member 14 (FIG. 4). The substantially V-shaped groove 108 functions as a hinge so that the opposed second end portion 48 of the handle member 14 can be angularly displaced relative to the longitudinal axis extending the length of the medial portion 46 of the handle member 14. Thus, the opposed second end portion 48 of the handle member 14 (which defines the gripping portion of the handle member 14) can be angularly displaced so as to be substantially parallel to the upper portion 28 of the specimen cup 18 for facilitating placement of the specimen cup 18 for receipt of a specimen.

Referring now to FIGS. 5A–5D, a second embodiment of a connector assembly 112 for connecting the handle member 14 to the extension member 38 of the specimen cup engaging assembly 12 is illustrated. The connector assembly 112, which connects the first end portion 44 of the handle member 14 to the extension member 38 of the specimen cup engaging assembly 12, comprises a male member 114 and a female member 116. The male member 114, which is connected to the distal end 54 of the extension member 38 so as to extend outwardly therefrom, is provided with a body portion 118 and an enlarged, wedge-shaped head portion 120. The distal end 54 of the extension member 38 is angularly disposed substantially as shown in FIG. 5C so that a shoulder 122 is formed at the junction of the distal end 54 of the extension member 38 and the body portion 118 of the male member 114. Further, the enlarged, wedge-shaped head portion 120 of the male member 114 cooperates with the shoulder 122 so that a recessed portion 124 is formed along an upper side 126 of the body portion 118 of the male member 114.

The configuration of the enlarged wedge-shaped head portion 120 of the male member 114 enables one to more easily insert the male member 114 into the female member 116 of the connector assembly 112; and the shoulder 122 and an edge 128 of the enlarged, wedge-shaped head portion 120 cooperate to secure the female member 116 in a stable position on the body portion 118 of the male member 114. That is, when the body portion 118 of the male member 114 is disposed in the female member 116, the shoulder 122 formed between the distal end 54 of the extension member 38 and the body portion 118 and the edge 128 of the enlarged wedge-shaped head portion 120 secure the handle member 14 to the extension member 38 of the specimen cup engaging assembly 12 and prevent inadvertent and unintentional removal of the handle member 14 therefrom.

The female member 116 of the connector assembly 112, which is supported by the first end portion 44 of the handle member 14, comprises a slot or opening 130 through which the enlarged wedge-shaped head portion 120 can be disposed so that the body portion 118 of the male member 114 is disposed in the slot 130. The dimensions of the slot 130 can vary, but the slot 130 is dimensioned to permit passage of the enlarged wedge-shaped head portion 120 therethrough, while preventing unintentional removal of the enlarged wedge-shaped head portion 120 and thus disconnection of the handle member 14 from the extension member 38 of the specimen cup engaging assembly 12.

As is more clearly shown in FIG. 5D, the slot 130 of the female member 116 is provided with a first end 132 and an opposed second end 134. The first and second ends 132, 134 of the slot 130 are beveled and substantially parallel so that when the male member 114 is matingly engaged with the female member 116 of the connector assembly 112, the handle member 14 is supported in the desired angular position relative to the ring member 36 of the specimen cup engaging assembly 12 substantially as shown. It should be noted that while the first and second ends 132, 134 of the slot 130 have been shown as being beveled, one can fabricate the slot 130 so that the first and second ends 132, 134 are parallel to each other and extend substantially perpendicular to the elongated axis of the handle member 14.

Referring now to FIGS. 6A–6C, another embodiment of a connector assembly 136 for connecting the handle member 14 to the extension member 38 of the specimen cup engaging assembly 12 is illustrated. The connector assembly 136, which connects the first end portion 44 of the handle member 14 to the extension member 38 of the specimen cup engaging assembly 12, comprises a male member 138 and a female member 140. The male member 138, which extends outwardly from the distal end 54 of the extension member 38, is provided with a body portion 142 and an arcuate shaped nipple portion 144.

The female member 140 of the connector assembly 136, which is supported by the first end portion 44 of the handle member 14, comprises a slot or opening 148 through which the arcuate shaped nipple portion 144 of the male member 138 can be disposed so that the body portion 142 of the male member 138 is disposed in the slot 148. The dimensions of the slot 148 can vary, as can its shape or configuration, provided the slot 148 is dimensioned to permit passage of the arcuate shaped nipple portion 144 therethrough, while preventing unintentional removal of the arcuate shaped nipple portion 144 and thus disconnection of the handle member 14 from the extension member 38 of the specimen cup engaging assembly 12. That is, the body portion 142 and the arcuate shaped nipple portion 144 of the male member 138 cooperate with the female member 140 to stabilize the handle member 14 in the desired angular disposition when the body portion 142 of the male member 138 is disposed in the opening 148 of the female member 140.

Referring now to FIGS. 7 and 8, the specimen cup holder 10 is illustrated having a connector assembly 150 for interconnecting the handle member 14 to the extension member 38 of the specimen cup engaging assembly 12. The connector assembly 150 comprises a male member 152 and a female member 154. The male member 152 is supported by the first end portion 44 of the handle member 14 and the female member 154 is supported by the distal end 54 of the extension member 38. The male and female members 152, 154 can be of any suitable configuration provided that the female member 154 is adapted to matingly receive and retain the male member 152 so that the first end portion 44 of the handle member 14 can be connected to the extension member 38 of the specimen cup engaging assembly 12 in the desired position.

The male member 152 is a substantially T-shaped member having a body portion 156 and an enlarged head portion 158. The body portion 156 has a width which is less than the width of the handle member 14. Thus, a recess 164 is formed between the first end portion 44 of the handle member 14 and the enlarged head portion 158 of the male member 152.

The female member 154 of the connector assembly 150, which is supported by the distal end 54 of the extension member 38, comprises a slot or opening 166 having a width at least equal to the width of the body portion 156 of the male member 152, but less than the width of the enlarged head portion 158. The slot 166 is further provided with a length at least equal to the width of the enlarged head portion 158 of the male member 152. Thus, to connect the handle member 14 to the extension member 38 of the specimen cup engaging assembly 12, one first separates the handle member 14 from the extension member 38 by breaking the linkage 80 extending between the male member 152 and the female member 154 of the connector assembly 150. Thereafter, the handle member 14 is rotated so that the enlarged head portion 158 of the male member 152 is aligned with the slot 166 in a lengthwise direction.

The enlarged head portion 158 of the male member 152 is then positioned through the slot 166 and thereafter the handle member 14 is rotated so that the enlarged head portion 158 of the male member 152 engages the portion of the female member 154 defining the slot 166 therein and secures the handle member 14 to the extension member 38 of the specimen cup engaging assembly 12.

While various configurations have been shown for both the male and female members of the connector assemblies employed to connect the first end portion 44 of the handle member 14 to the distal end 54 of the extension member 38 of the specimen cup engaging assembly 12, it should be understood that any suitable configuration can be employed provided that the female member matingly receives the male member and secures the male member thereto in a stable position. Further, while certain slots of the female member have been shown having beveled ends, such as the slot 72 in the handle member 14 (FIG. 3A), one should understand that the male member can also be provided with a beveled surface in order to enhance the positioning and stabilization of the handle member relative to the specimen cup engaging assembly. For example, the male member can be beveled along its rearward extending portion, such as the rearwardly extending portion 66 of the outwardly extending retaining members 68, 70 of the male connector (FIG. 2B). The shoulder 122 formed at the junction of the distal end 54 of the extension member 38 and the body portion 118 of the male member 114 (FIG. 5C) can be beveled; or the rearwardly disposed edge 128 of the enlarged, wedge-shaped head portion 120 (FIG. 5C) can be beveled, all without departing form the inventive concept of the present invention.

Further, the specimen cup holder 10 of the present invention can be fabricated of any suitable material possessing sufficient strength to support the specimen cup 18 and specimens deposited therein. While numerous materials may be commercially available from which the specimen cup holder 10 can be fabricated, especially desirable results have been obtained wherein the specimen cup holder 10 is fabricated of a polyolefin.

Should it be necessary in order to provide additional strength to the specimen cup holder, conventional ribbing can be provided in the extension member 38 of the specimen cup engaging assembly 12 and the handle member 14. The use of reinforcing rib members in the construction of articles from polymeric materials, such as polyolefins, is well known in the art and thus no further comments concerning same are believed necessary in order to permit one to fully understand the inventive concepts set forth herein.

From the foregoing description, it is clear that the present invention is well adapted to carry out the objects and attain the ends and advantages mentioned as well as those inherent therein. While presently preferred embodiments of the invention have been described for purposes of this disclosure, numerous changes may be made which will readily suggest themselves to those skilled in the art, which changes are encompassed within the spirit of the invention disclosed and as defined in the appended claims herein.

What is claimed is:

1. A specimen cup holder comprising:
   specimen cup engaging means for supportingly engaging a specimen cup in a stable, specimen receiving position, the specimen cup engaging means having an opening therein for receiving and supporting a specimen cup;
   a handle member having a first and an opposed second end portion;
   first connector means for connecting the first end portion of the handle member to the specimen cup engaging means such that the opposed second end portion of the handle member extends outwardly from the specimen cup engaging means and provides a gripping portion so that a person grasping the gripping portion of the handle member can position a specimen cup disposed within the opening of the specimen cup engaging means for receipt of a specimen without contact with the specimen, the first connector means comprising:
      a female member having a male-receiving opening therein, the female member supported by either the specimen cup engaging means or the first end portion of the handle member; and
      a male member positionable within the male-receiving opening, the male member supported by the other of the specimen cup engaging means or the first end portion of the handle member, the male member having a retaining means for abuttingly engaging the female member when the male member is positioned through the male-receiving opening of the female member for connecting the handle member to the specimen cup engaging means; and
   hinge means supported by the handle member and located a selected distance from the opposed second end portion of the handle member such that the gripping portion defined by the opposed second end portion of the handle member can be disposed substantially parallel to an upper portion of a specimen cup supported within the opening of the specimen cup engaging means for facilitating placement of a specimen cup for receipt of a specimen.

2. The specimen cup holder of claim 1 wherein the hinge means comprises a substantially V-shaped notch formed in a lower side of the handle member, the V-shaped notch being normally disposed relative to an elongated axis extending the length of the handle member.

3. The specimen cup holder of claim 1 wherein the female member of the first connector means is supported by the first end portion of the handle member, the male member of the first connector means is supported by the extension member of the specimen cup engaging means and wherein the male receiving opening of the female member is characterized as having a first end and an opposed second end which are substantially parallel relative to one another, and wherein the handle member is provided with a longitudinally extending slit openly communicating with the male receiving opening of the female member.

4. The specimen cup holder of claim 3 further comprising:
second connector means comprising two opposed connector members for connecting the first end portion of the handle member to the extension member of the specimen cup engaging means when the first connector means is in a disassembled position while also permitting the handle member to be selectively rotated in order to connect the handle member to the specimen cup engaging means via the first connector means.

5. A specimen cup holder comprising:
specimen cup engaging means for supportingly engaging a specimen cup in a stable, specimen-receiving position, the specimen cup engaging means having an opening therein for receiving and supporting a specimen cup and having an extension member;
a handle member having a first end portion and an opposed second end portion; and
first connector means for connecting the first end portion of the handle member to the extension member of the specimen cup engaging means such that the opposed second end portion of the handle member extends outwardly from the specimen cup engaging means and provide a gripping portion so that a person grasping the gripping portion can position a specimen cup disposed within the opening of the specimen cup engaging means for receipt of a specimen without contact with the specimen, the first connector means comprising:
a female member supported by the first end portion of the handle member, the female member having a male-receiving opening therein, the male-receiving opening characterized as having first and second opposed ends which are bevelled and disposed substantially parallel with one another; and
a male member supported by the extension member of the specimen cup engaging means so as to be positionable within the male-receiving opening of the female member such that, in a connected position, the female and male members cooperate to secure the handle member to the extension member of the specimen cup engaging means while supporting the handle member at an angle relative to the opening in the specimen cup engaging means.

6. A specimen cup holder comprising:
specimen cup engaging means for supportingly engaging a specimen cup in a stable, specimen-receiving position;
a handle member having a first end portion and an opposed second end portion;
first connector means for connecting the first end portion of the handle member to the specimen cup engaging means such that the opposed second end portion of the handle member extends outwardly from the specimen cup engaging means and provides a gripping portion so that a person grasping the gripping portion can position a specimen cup supported by the specimen cup engaging means for receipt of a specimen without contact with the specimen; and
second connector means comprising two opposed connector members for connecting the first end portion of the handle member to the specimen cup engaging means when the first connector means is in a disassembled position while also permitting the handle member to be selectively rotated in order to connect the handle member to the specimen cup engaging means via the first connector means.

7. A specimen cup holder comprising:
specimen cup engaging means for supportingly engaging a specimen cup in a stable, specimen-receiving position, the specimen cup engaging means comprising:
a ring member having an opening therein for receiving and supporting a specimen cup; and
an extension member extending from the ring member;
a handle member having a first end portion and an opposed second end portion; and
first connector means for connecting the first end portion of the handle member to the extension member of the specimen cup engaging means such that the opposed second end portion of the handle member extends outwardly from the ring portion of the specimen cup engaging means and provides a gripping portion so that a person grasping the gripping portion can position a specimen cup supported within the opening of the ring member of the specimen cup engaging means for receipt of a specimen without contact with the specimen, the first connector means comprising:
a female member extending from a distal end portion of the extension member of the specimen cup engaging means, the female member having a male-receiving opening therein; and
a male member extending from the first end portion of the handle member, the male member positionable within the male-receiving opening, the male member having a retaining means for abuttingly engaging the female member when the male member is positioned through the male-receiving opening of the female member so as to secure the handle member to the specimen cup engaging means.

8. The specimen cup holder of claim 7 further comprising:
hinge means supported by the handle member and located a selected distance from the opposed second end portion thereof such that the gripping portion defined by the opposed second end portion of the handle member can be disposed substantially parallel to an upper portion of a specimen cup supported within the opening of the ring member of the specimen cup engaging means.

9. The specimen cup holder of claim 8 wherein the hinge means comprises a substantially V-shaped notch formed in a lower side of the handle member, the V-shaped notch being normally disposed relative to an elongated axis extending the length of the handle member.

10. A specimen cup holder comprising:
specimen cup engaging means for supportingly engaging a specimen cup in a stable, specimen-receiving position, the specimen cup engaging means comprising:
a ring member having an opening therein for receiving and supporting a specimen cup; and
an extension member extending from the ring member, the extension member having a distal end portion;

a handle member having a first end portion, a medial portion and an opposed second end portion, the first end portion of the handle member connectable to the extension member of the specimen cup engaging means such that the second end portion of the handle member extends outwardly from the ring member of the specimen cup engaging means so that a specimen cup supported within the opening of the ring member of the specimen cup engaging means can be positioned for receipt of a specimen without contact with the specimen by a person gripping the second end portion of the handle member;

first connector means for detachably connecting the first end portion of the handle member to the extension member of the specimen cup engaging means, the first connector means comprising:

a female member extending from the first end portion of the handle member and having a male-receiving opening therein; and a male member extending from the distal end portion of the extension member of the specimen cup engaging means and positionable within the male-receiving opening, the male member having a retaining lip portion such that, upon positioning the male member through the male-receiving opening of the female member, the retaining lip portion of the male member abuttingly engages the female member and secures the first end portion of the handle member to the distal end portion of the extension member of the specimen cup engaging means; and hinge means supported by the handle member so as to be disposed between the second end portion of the handle member and the adjacently disposed medial portion of the handle member such that the second end portion of the handle member defines a gripping portion which is disposed substantially parallel to an upper portion of a specimen cup supported within the opening of the ring member of the specimen cup engaging means.

11. The specimen cup holder of claim 10 further comprising:

second connector means comprising two opposed connector members for connecting the first end portion of the handle member to the extension member of the specimen cup engaging mans when the first connector means is in a disassembled position while also permitting the handle member to be selectively rotated in order to connect the handle member to the specimen cup engaging means via the first connector means.

12. A specimen cup holder comprising:

specimen cup engaging means for supportingly maintaining a specimen cup in a stable, specimen-receiving position, the specimen cup engaging means comprising:

a ring member having an opening therein for receiving and supporting a specimen cup;

an extension member extending from the ring member, the extension member characterized as having a distal end portion;

a handle member having a first end portion, and a medial portion and an opposing second end portion;

first connector means for detachably connecting the first end portion of the handle member to the extension member of the specimen cup engaging means, the first connector means comprising:

a female member extending from the distal end portion of the extension member of the specimen cup engaging means, the female member having a male-receiving opening formed therein; and p2 a male member extending from the first end portion of the handle member, the male member having a retaining lip such that upon positioning the male member through the male-receiving opening of the female member, the retaining lip of the male member abuttingly engages the female member and secures the first end portion of the handle member to the extension member of the specimen cup engaging means such that the second end portion of the handle member extends outwardly from the ring member of the specimen cup engaging means so that a specimen cup supported within the opening in the ring member of the specimen cup engaging means can be positioned for receipt of a specimen without contact with the specimen by a person gripping the second end portion of the handle member.

13. The specimen cup holder of claim 12 further comprising:

hinge means supported by the handle member so as to be disposed between the medial portion of the handle member and the second end portion thereof for providing the second end portion of the handle member with a gripping portion which can be disposed substantially parallel to an upper portion of a specimen cup supported within the opening of the ring member of the specimen cup engaging means.

14. The specimen cup holder of claim 13 further comprising:

second connector means comprising two opposed connector members for connecting the first end portion of the handle member to the extension member of the specimen cup engaging means when the first connector means is in a disassembled position while also permitting the handle member to be selectively rotated in order to connect the handle member to the specimen cup engaging means via the first connector means.

15. A specimen cup holder comprising:

specimen cup engaging means for supportingly engaging a specimen cup in a stable, specimen-receiving position;

a handle member connectable to the specimen cup engaging means so that the handle member extends outwardly from the specimen cup engaging means;

a female connector member having a male-receiving opening and an elongated slit openly communicating with the male-receiving opening, the female connector member supported by either the specimen cup engaging means or the handle member; and a male connector member positionable within the male-receiving opening, the male connector member supported by the other of the specimen cup engaging means or the handle member such that in a connected position the male connector member matingly engages the female connector member and secures the handle member to the specimen cup engaging means so that a specimen cup supported within the specimen cup engaging means can be positioned for receipt of a specimen without contact with a specimen by a person gripping the handle member.

* * * * *